US007593559B2

(12) United States Patent
Toth et al.

(10) Patent No.: US 7,593,559 B2
(45) Date of Patent: Sep. 22, 2009

(54) METHOD AND SYSTEM OF COREGISTRATING OPTICAL COHERENCE TOMOGRAPHY (OCT) WITH OTHER CLINICAL TESTS

(75) Inventors: Cynthia A. Toth, Chapel Hill, NC (US); Marcin Stopa, Poznan (PL); Bradley A. Bower, Hillsborough, NC (US)

(73) Assignee: Duke University, Durham, NC (US)

( * ) Notice: Subject to any disclaimer, the term of this patent is extended or adjusted under 35 U.S.C. 154(b) by 35 days.

(21) Appl. No.: 11/600,913

(22) Filed: Nov. 17, 2006

(65) Prior Publication Data

US 2007/0115481 A1 May 24, 2007

Related U.S. Application Data

(60) Provisional application No. 60/737,776, filed on Nov. 18, 2005.

(51) Int. Cl.
*G06K 9/00* (2006.01)
(52) U.S. Cl. .......................... 382/128; 128/922; 378/4; 351/200
(58) Field of Classification Search ................ 382/100, 382/117, 128, 130, 131, 151, 154, 190, 191, 382/195, 203, 280, 294; 351/200; 378/4–27
See application file for complete search history.

(56) References Cited

U.S. PATENT DOCUMENTS

| | | | | |
|---|---|---|---|---|
| 4,253,743 A | * | 3/1981 | Matsumura ................. | 351/208 |
| 4,715,703 A | * | 12/1987 | Cornsweet et al. .......... | 351/205 |
| 4,952,050 A | * | 8/1990 | Aizu et al. .................. | 351/221 |
| 5,037,194 A | * | 8/1991 | Kohayakawa et al. ....... | 351/224 |
| 5,347,331 A | * | 9/1994 | Isogai et al. ................ | 396/18 |
| 5,691,800 A | * | 11/1997 | Iki et al. .................... | 351/212 |
| 5,767,940 A | * | 6/1998 | Hayashi et al. ............. | 351/205 |
| 5,836,877 A | * | 11/1998 | Zavislan .................... | 600/407 |
| 5,989,189 A | * | 11/1999 | LeBlanc et al. ............. | 600/437 |
| 6,266,435 B1 | * | 7/2001 | Wang ......................... | 382/132 |
| 6,434,262 B2 | * | 8/2002 | Wang ......................... | 382/132 |
| 7,178,099 B2 | | 2/2007 | Meyer et al. | |
| 7,301,644 B2 | * | 11/2007 | Knighton et al. ............ | 356/479 |
| 2005/0094099 A1 | * | 5/2005 | Newman et al. ............ | 351/205 |

OTHER PUBLICATIONS

Wojtkowski et al. (Maciej Wojtkowski, Vivek Srinivasan, James G. Fujimoto, et al., "Three-dimensional retinal imaging with high-speed ultrahigh-resolution optical coherence tomography," Ophthalmology Oct. 10, 2005; vol. 112 pp. 1734-1746).*

(Continued)

*Primary Examiner*—Anand Bhatnagar
(74) *Attorney, Agent, or Firm*—Nixon & Vanderhye P.C.

(57) ABSTRACT

A method/system preserves annotations of different pathological conditions or changes that are recognized on cross-sections within a three dimensional volume of a patient's eye so that the annotations are maintained in a visible state in an en face projection produced with a SVP technique. it is thus possible to coregister the annotated conditions or changes with other types of two dimensional en face images such as images from other ophthalmic devices (e.g., angiography device, microperimetry device, autofluorescence device, fundal photography device.). The annotations are also maintained in a visible state in the coregistered image.

46 Claims, 10 Drawing Sheets

OTHER PUBLICATIONS

Pieroni CG, Witkin AJ, Ko TH, et al., "*Ultrahigh resolution optical coherence tomography in non-exudative age related macular degeneration*," Br J Ophthalmol 2006;90(2):191-7.

Massin P, Girach A, Erginay A, Gaudric A., "*Optical coherence tomography: a key to the future management of patients with diabetic macular oedema*," Acta Ophthalmol Scand 2006;84(4):466-74.

Huang D, Swanson EA, Lin CP, et al., "*Optical coherence tomography*," Science 1991;254:1178-81.

Puliafito CA, Hee MR, Lin CP, et al., "*Imaging of macular diseases with optical coherence tomography*," Ophthalmology 1995;102:217-29.

Hee MR, Izatt JA, Swanson EA, et al., "*Optical coherence tomography of the human retina*," Arch Ophthalmol 1995;113:325-32.

Wojtkowski M, Bajraszewski T, Gorczyńska I, et al., "*Ophthalmic imaging by spectral optical coherence tomography*," Am J Ophthalmol 2004;138:412-9.

Wojtkowski M, Leitgeb R, Kowalczyk A, et al., "In vivo *human retinal imaging by Fourier domain optical coherence tomography*," J Biomed Opt 2002;7:457-63.

Wojtkowski M, Bajraszewski T, Targowski P, Kowalczyk A., "*Real-time* in vivo *imaging by high-speed spectral optical coherence tomography*," Opt Lett 2003;28:1745-7.

Wojtkowski M, Srinivasan V, Fujimoto JG, et al., "*Three-dimensional retinal imaging with high-speed ultrahigh-resolution optical coherence tomography*," Ophthalmology 2005;112:1734-46.

Jiao S, Knighton R, Huang X, et al., "*Simultanous acquisition of sectional and fundus ophthalmic images with spectral-domain optical coherence tomography*," Optics Express 2005;13:444-52.

Zawadzki RJ, Jones SM, Olivier SS, et al., "*Adaptive-optics optical coherence tomography for high-resolution and high-speed 3D retinal* in vivo *imaging*," Optics Express 2005;17:8532-46.

Abramoff MD, Magelhaes PJ, Ram SJ., "*Image Processing with ImageJ*," Biophotonics International 2004;11:36-42.

Bressler NM, Bressler SB, Alexander J, et al., "*Loculated fluid. A previously undescribed fluorescein angiographic finding in choroidal neovascularization associated with macular degeneration*," Macular Photocoagulation Study Reading Center. Arch Ophthalmol 1991;109:211-5.

Soubrane G, Coscas G, Larcheveque F., "*Macular Degeneration related toage and cystoid macular edema [in French]*," Apropos of 95 cases (100 eyes). J Fr Ophthalmol 1988;11:711-20.

Podoleanu AG, Dobre GM, Cucu RG, et al., "*Combined multiplanar optical coherence tomography and confocal scanning ophthalmoscopy*," J Biomed Opt 2004;9:86-93.

Van Velthoven MEJ, de Vos K, Verbraak FD, et al., "*Overlay of conventional angiographic and en-face OCT images enhances their interpretation*," BMC Ophthalmol 2005;5:12.

Van Velthoven MEJ, Verbraak FD, Garcia PM, et al., "*Evaluation of central serous retinopathy with en face optical coherence tomography*," Br J Ophthalmol 2005;89:1483-8.

Van Velthoven MEJ, Verbraak FD, Yannuzzi L, et al., "*Imaging the retina by en face optical coherence tomography*," Retina 2006;26:129-36.

Podoleanu AG, Rogers JA, Jackson DA., "*3D OCT images from retina and skin*," Optics Express 2000;7:292-8.

Nassif et al, "In vivo *human retinal imaging by ultrahigh-speed spectral domain optical coherence tomography*", Optics Letters 29:480-482 (2004).

International Search Report issued in international application No. PCT/US06/44534 on Apr. 3, 2008.

Written Opinion of the International Searching Authority issued in international application No. PCT/US06/44534 on Apr. 3, 2008.

"Defining Through Verbal Charades" English Language Arts Resources, Public Schools of North Carolina, http://www.ncpublicschools.org/curriculum/languagearts/secondary/rightdirection2/15color. . . (downloaded 2008).

\* cited by examiner

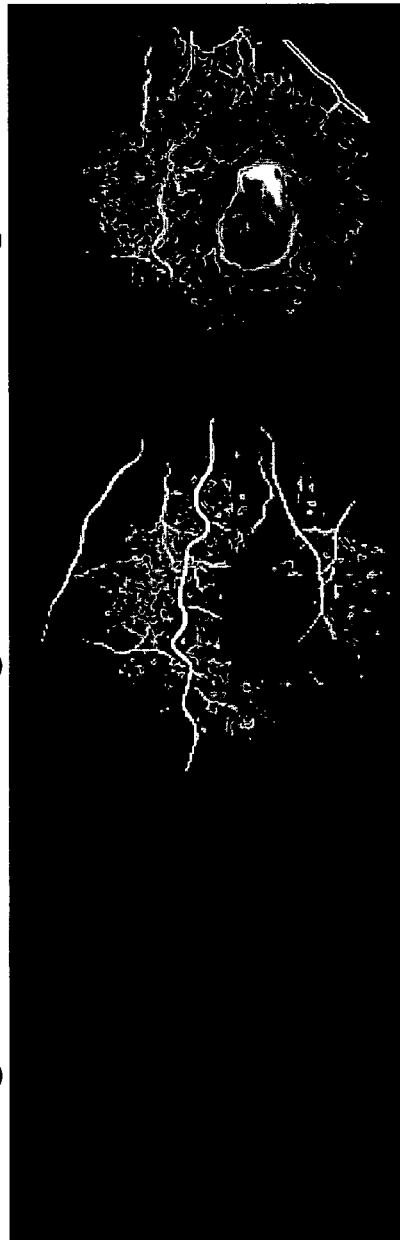
Fig. 6C
Fig. 6B
Fig. 6A
Fig. 6D
Fig. 6E

Fig. 7A
Fig. 7B
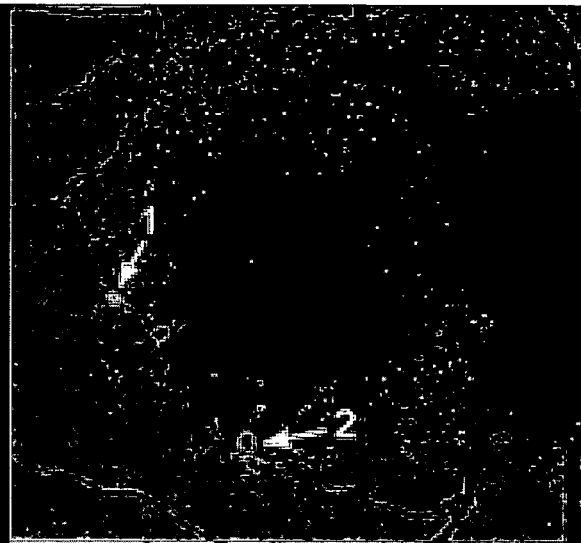
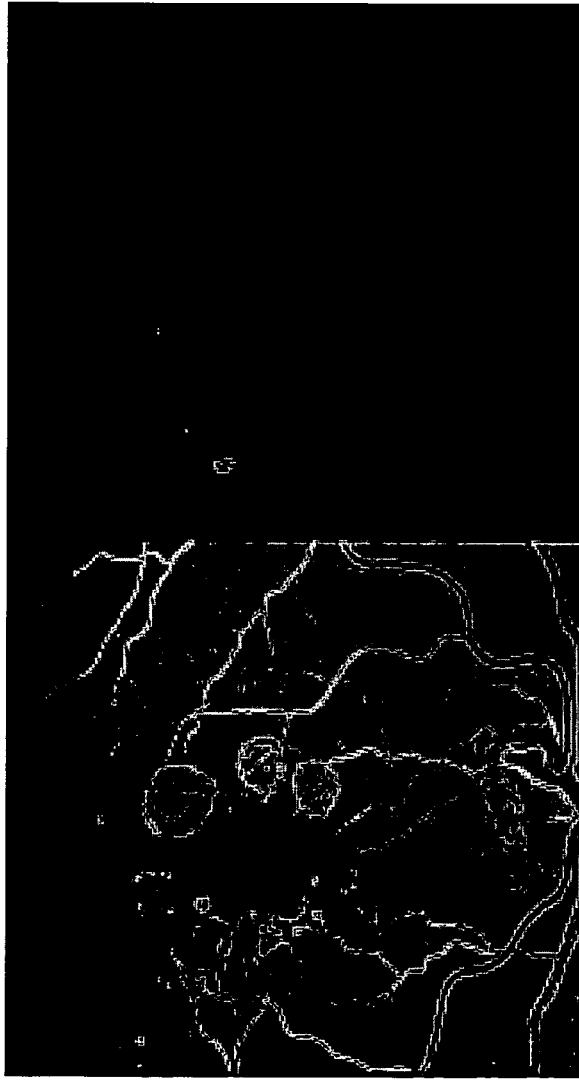
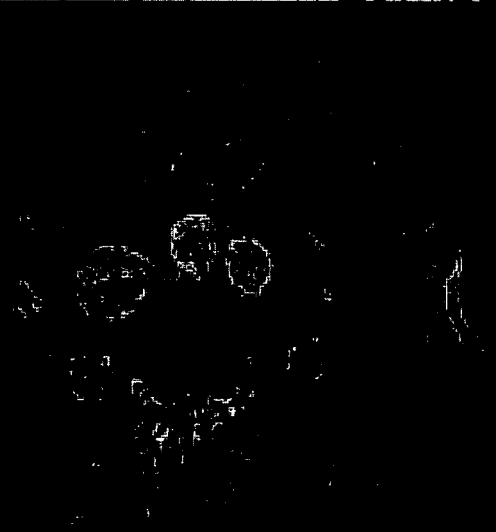
Fig. 7C
Fig. 7D

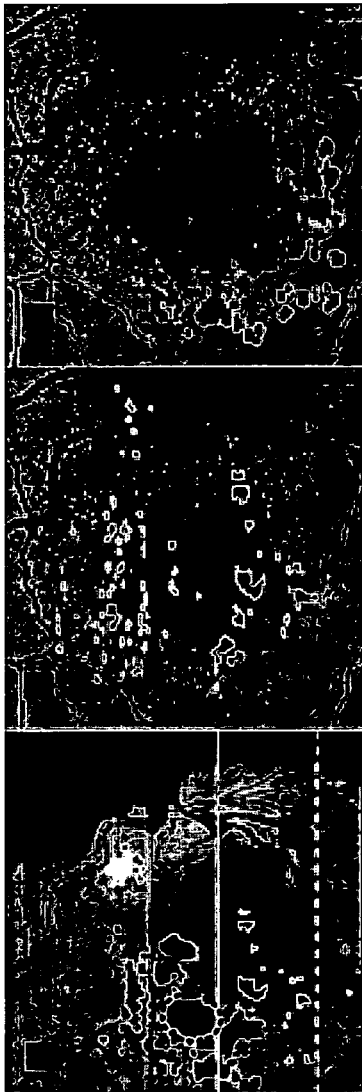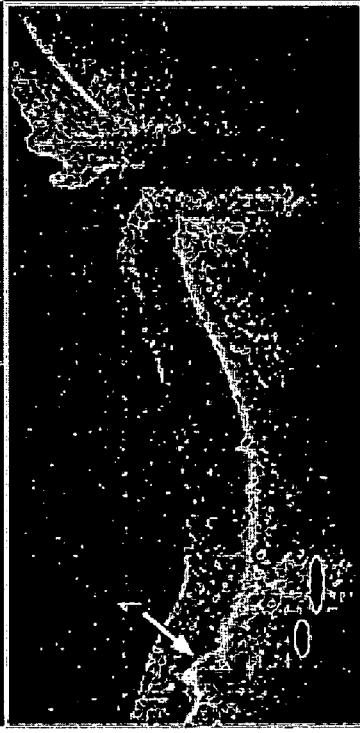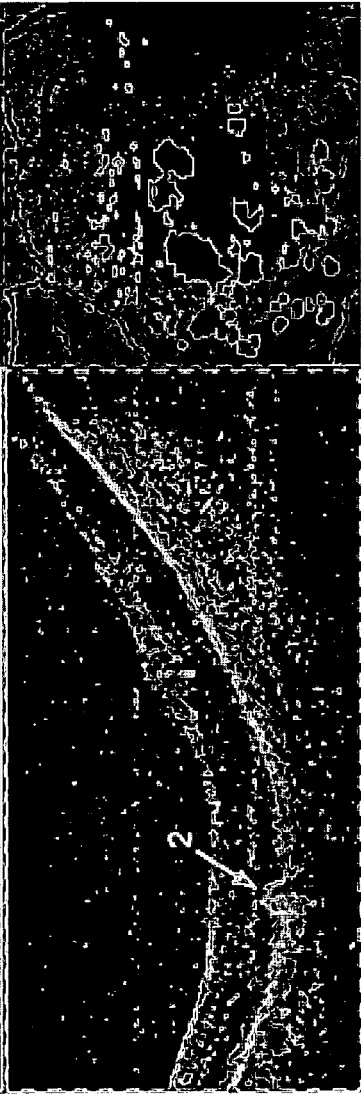

Fig. 9A
Fig. 9B
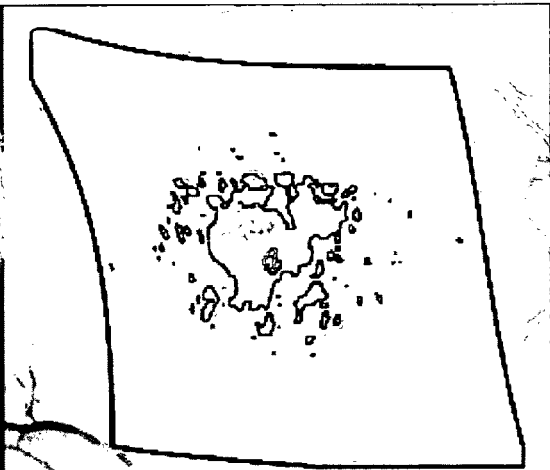
Fig. 9C
Fig. 9D
Fig. 9E
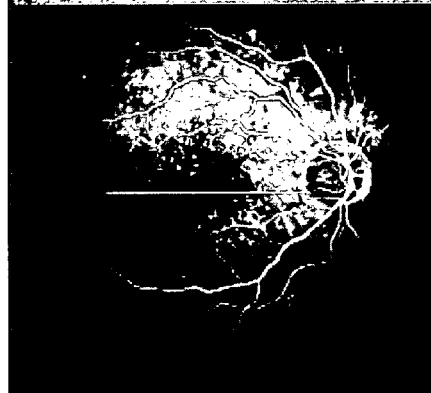
Fig. 9F

METHOD AND SYSTEM OF COREGISTRATING OPTICAL COHERENCE TOMOGRAPHY (OCT) WITH OTHER CLINICAL TESTS

CROSS REFERENCE TO RELATED APPLICATION

This application claims priority from U.S. Provisional Application 60/737,776 filed Nov. 18, 2005, the entire content of which is incorporated herein by reference.

STATEMENT OF FEDERAL SPONSORED RESEARCH

This invention was made with government support under grants EB000243 and RR019769 awarded by the National Institutes of Health. The government has certain rights in the invention.

TECHNICAL FIELD

Exemplary embodiments of the present technology relate to a method and system of image processing and analysis. In particular, the present method/system preserves an annotation of pathology in a summed voxel projection (SVP) of a series of scans (for instance, from optical coherence tomography) for use in coregistration with data from other technologies such as ophthalmic imaging.

BACKGROUND AND SUMMARY

Clinicians and researchers continue to need better methods to gather biologically incisive data on retinal disease and in vivo pathology. There currently exists no satisfactory method or system to localize focal in vivo pathology that correlates with function. Retinal imaging with optical coherence tomography (OCT) has improved over the past decade and yields cross-sectional images of retinal morphology. (See Pieroni C G, Witkin A J, Ko T H, et al., "*Ultrahigh resolution optical coherence tomography in non-exclusive age related macular degeneration*," Br J Ophthalmol 2006; 90(2): 191-7; and Massin Girach A, Erginay A, Gaudric A., "*Optical coherence tomography: a key to the future management of patients with diabetic macular oedema*," Acta Ophthalmol Scand 2006; 84(4): 466-74.) Although clinicians are able to define pathologies on retinal OCT cross-sections based on previous clinicopathologic correlation, this cross-sectional information is viewed separately and not integrated with conventional fundus imaging such as color photography and angiography. Although thickness data calculated from cross-sectional scans have been converted and interpolated into surface maps of the macula or of nerve fiber layer thicknesses, these maps rely on location of scans as judged by fundus video images or on fixation. Consequently, they lack annotation of focal pathology.

Spectral domain optical coherence tomography (SD-OCT), also known as Fourier domain OCT, is a relatively new imaging technique that utilizes the Fourier transform function to gather depth data from the spectra of the OCT signal and thus eliminates the need to mechanically move the scanning mirror to obtain depth information as is required for commercially available time-domain systems. (See Huang D, Swanson E A, Lin C P, et al., "*Optical coherence tomography*," Science 1991;254:1178-81; Puliafito C A, Hee M R, Lin C P, et al., "*Imaging of macular diseases with optical coherence tomography*," Ophthalmology 1995;102:217-29; and Hee M R, Izatt J A, Swanson E A, et al., "*Optical coherence tomography of the human retina*," Arch Ophthalmol 1995;113:325-32.) The SD-OCT technique significantly increases signal-to-noise ratio and increases the speed of data collection by a factor of 50 (conventional time-domain OCT functions at 400 A-scan/sec, while the SD-OCT system scans at 20,000 A-scan/sec). (See Wojtkowski M, Bajraszewski T, Gorczyńska I, et al., "*Ophthalmic imaging by spectral optical coherence tomography*," Am J Ophthalmol 2004;138:412-9; Wojtkowski M, Leitgeb R, Kowalczyk A, et al., "*In vivo human retinal imaging by Fourier domain optical coherence tomography*," J Biomed Opt 2002;7:457-63; and Wojtkowski M, Bajraszewski T, Targowski P, Kowalczyk A., "*Real-time in vivo imaging by high-speed spectral optical coherence tomography*," Opt Lett 2003;28:1745-7.) Because of the increase in speed, a single cross-sectional scan of 1000 A-scans can be captured, processed, streamed to disk, and displayed in 60 ms (or 1/42 of the time required for a time-domain scan). Because of this speed, there is less eye movement during the SD-OCT scan and thus a more stable image with a significant decrease in artifact of the image caused by patient motion. Also because of this speed, a stack of 100 cross-sectional scans can be acquired in the time normally used to gather 6 low resolution cross-sectional scans of the macula on a time-domain system. The image stack across the macula can be processed to produce a three dimensional representation of structures. (See Wojtkowski M, Srinivasan V, Fujimoto J G, et al., "*Three-dimensional retinal imaging with high-speed ultrahigh-resolution optical coherence tomography*," Ophthalmology 2005;112:1734-46.)

SD-OCT imaging thus frequently uses a series of scans. A resulting stack of B-scans can undergo further analysis and produce a three dimensional representation of structures. Furthermore, it is possible to collapse three dimensional OCT volumes (e.g., along a depth axis) to a two-dimensional representative image along any plane of a 3D volume using algorithms to calculate a single representative pixel intensity for each line in the projection. One technique of obtaining such an en face picture with optical coherence tomograms is referred to as a summed voxel projection (SVP). (See Jiao et al, "*Simultaneous acquisition of sectional and fundus ophthalmic images with spectral-domain optical coherence tomography*", Optics Express 13:444-452 (2005)).

Even though some pathological structures can be observed on a two dimensional en face image produced with SVP, this technique may not show all the changes that might be relevant for the diagnosis because some information is lost. In particular, the SVP technique may not show relevant pathologies because much information is lost in the summing of the pixels in the collapsing process.

Accordingly, there is a need for an exact system/method to annotate, extract and preserve different pathological conditions and/or changes that are recognized on cross-sections within the three dimensional volume so that the findings are maintained (preserved as visible) in an en face projection produced with a SVP technique. Exemplary embodiments of the technology described herein resolve such a need.

Present exemplary embodiments provide a method/system to annotate, extract or preserve different pathological conditions and/or changes that are recognized on cross-sections within a three dimensional volume so that the findings are maintained (preserved as visible) in an en face projection produced with a SVP technique. Furthermore, present exemplary embodiment(s) make it possible to coregister marked changes with other types of two dimensional en face images such as images from other ophthalmic devices (e.g., angiography device, microperimetry device, autofluorescence device, fundal photography device, etc.). The findings are maintained in an image resulting from a coregistration of the projection produced with the SVP technique and the other types of two dimensional en face images.

In more detail, present exemplary embodiments delineate, extract and preserve different pathological conditions and/or changes that are recognized on retinal cross-sections obtained from patients with retinal disease. The patients may have, for example, neovascular and non neovascular age related macular degeneration (AMD). With present exemplary embodiments, the delineated pathology (e.g., pathology delineated, via color-coded markings or sets of numbers, by a user and/or automatically by an image processing, rendering and interpolation algorithm) remains visible through the SVP and coregistration process. Thus the lateral extent and location of pathology (as well as other features of the pathology such as thickness, volume, size and/or severity) is precisely maintained relative to retinal vasculature on fundus images produced with the SVP technique.

The present exemplary embodiments thus identify, quantify and locate pathologic conditions and/or changes in retinal cross-sections obtained with SD-OCT so that the findings are maintained when collapsed into a two-dimensional fundus image for comparison with other retinal studies. These findings are also maintained during coregistration of the SD-OCT image data with other retinal study (e.g., angiography, microperimetry, autofluorescence and/or fundal photography) data. Alignment of the SD-OCT and other study image data during their coregistration may be obtained via a common location (e.g., location of pathology or distinguishable vascular landmark) identified by the user and/or system.

BRIEF DESCRIPTION OF THE DRAWINGS

FIG. 4A is an image resulting from a coregistration process having Fluorescein angiography (70 s) with superimposed margins of morphological change identified in the SD-OCT of FIG. 3C.

FIG. 4B is an image resulting from a coregistration process having microperimetry tested at 44 points with overlay of corresponding color landmarks resulting from the SD-OCT of FIG. 3C. Empty squares represent a not seen stimulus, whereas filled squares represent seen stimulus. Threshold values (in dB) are reported besides each stimulus. Lower values correspond to decreased sensitivity.

FIGS. 6A-6E are retinal images of the right eye of patient 1. A color fundus photo (FIG. 6A), fluorescein angiogram images taken at 27 seconds (FIG. 6B) and at 5 minutes 45 seconds (FIG. 6C), a horizontal StratusOCT scan through the fovea (FIG. 6D), and a vertical StratusOCT scan through the fovea (FIG. 6E) are illustrated.

FIGS. 7A-7D are retinal images, including an Heidelberg autofluorescence image (FIG. 7B) and fluorescein angiographs (FIGS. 7C, 7D) from the right eye of patient 2, enlarged to show drusen and geographic atrophy. A color fundus photo is dim due to cataracts in FIG. 7A. In FIG. 7B, site #1 is shown on autofluorescence and corresponds to a drusen with high reflectivity at the inner surface and extending into the overlying retina, and site #2 is shown on autofluorescence and corresponds to a drusen with unusual OCT reflectivity pattern. SD-OCT B-scans from these sites are shown in FIGS. 8D and 8F.

FIGS. 8A-8G illustrate the summed voxel projection of OCT data with overlay of color markings from the right eye of patient 2 (FIG. 8A). The solid yellow line delineates the site of the SD-OCT B-scan corresponding to site #1 from FIG. 7B (FIG. 8D). The dotted yellow line delineates the site of the SD-OCT B-scan corresponding to site #2 from FIG. 7B (FIG. 8F). Teal green markings of indistinct drusen overlayed onto autofluorescence are illustrated in FIG. 8B. Magenta markings of distinct drusen overlayed onto autofluorescence are illustrated in FIG. 8C. Light purple markings of geographic atrophy overlayed onto autofluorescence are illustrated in FIG. 8E. Autofluorescence with overlay of all markings are illustrated in FIG. 8G.

FIGS. 9A-9F illustrate summed voxel projections and outlines of marked pathology warped to color fundus photo of the right eye of a patient with non-neovascular AMD. The SVP of the 10 mm×10 mm SD-OCT scans with brightness and contrast auto-corrected has less resolution of small retinal vessels in FIG. 9A, compared to the SVP of the 5 mm×5 mm SD-OCT scans in FIG. 9C. The excellent resolution of small retinal vessels in FIG. 9C is useful for overlay and correlation with retinal images. Outlines of marked drusen and drusenoid PED (black) and subretinal fluid (blue) created from stack of SD-OCT B-scans are warped to a color fundus photo for overlay with the 10 mm×10 mm scan in FIG. 9B and the 5 mm×5 mm scan in FIG. 9D. A fluorescein angiogram taken at 4 minutes, 16 seconds is illustrated in FIG. 9E. The yellow line delineates location of an SD-OCT B-scan that shows subretinal fluid at the fovea above drusenoid PED in FIG. 9F.

DETAILED DESCRIPTION OF PRESENT EXEMPLARY EMBODIMENTS

Figure 1:
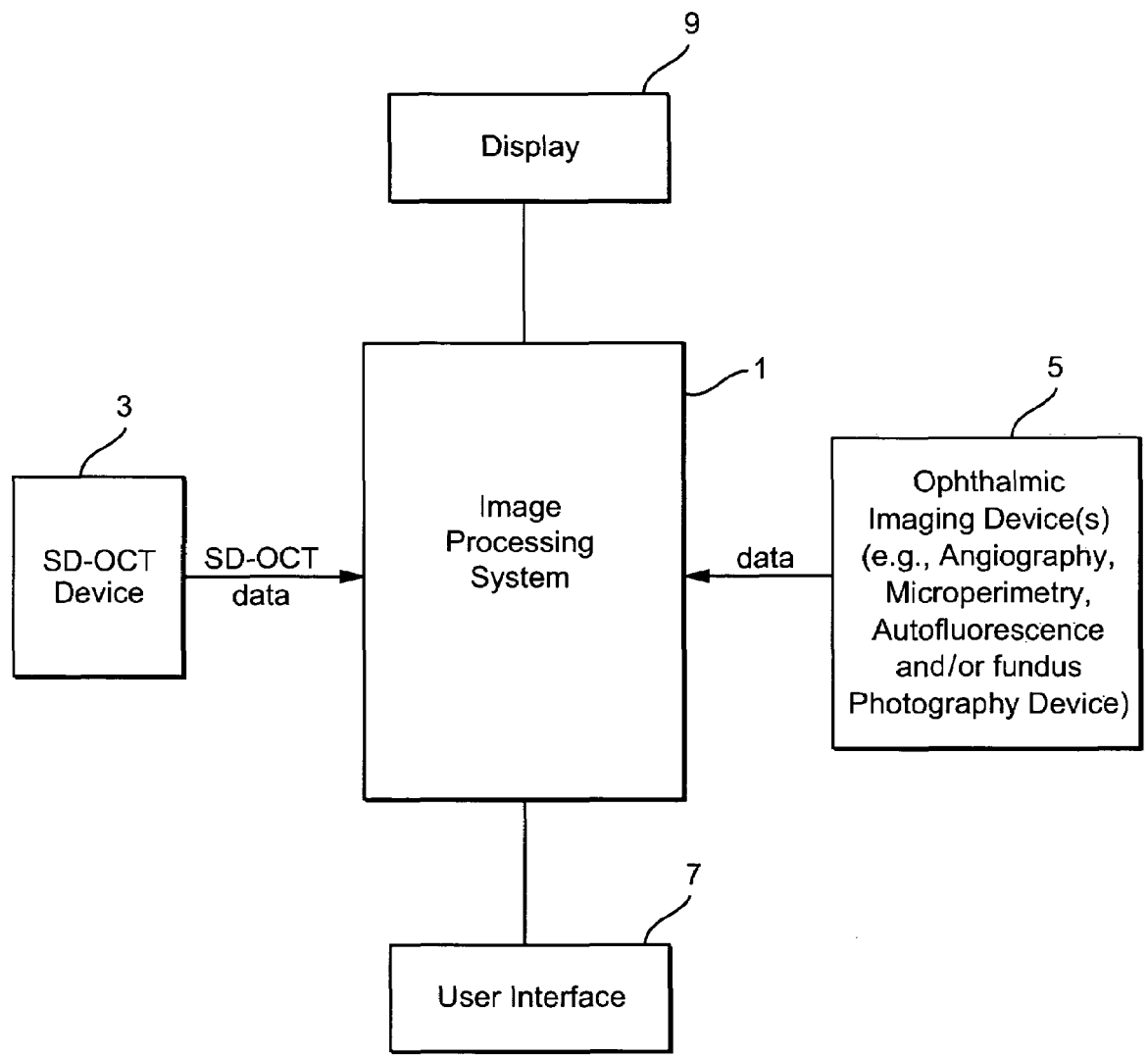
FIG. 1 is a diagram of a system for performing co-registration of a SVP image of marked SD-OCT image data with an image from other imaging device(s) such as ophthalmic device(s) in accordance with a present exemplary embodiment.

FIG. 1 illustrates an exemplary system having an image processing system 1. The image processing system 1 comprises a computer having processing components, storage memories, etc. The image processing system 1 receives imaging data from an SD-OCT scanning device 3 and from one or more ophthalmic device(s) such as an angiography, autofluorescence, fundal photography and/or microperimetry device 5. A user (e.g., ophthalmologist, radiologist, etc.) may provide input to the image processing system 1 through a user interface 7 (e.g., a keyboard and/or mouse). An output of the image processing system 1 is stored in for example a memory of the system 1 and may be displayed on display 9 or on a hard copy through operation of a printer (not shown). The processing performed by the image processing system may be partially or fully automated.

Figure 2:
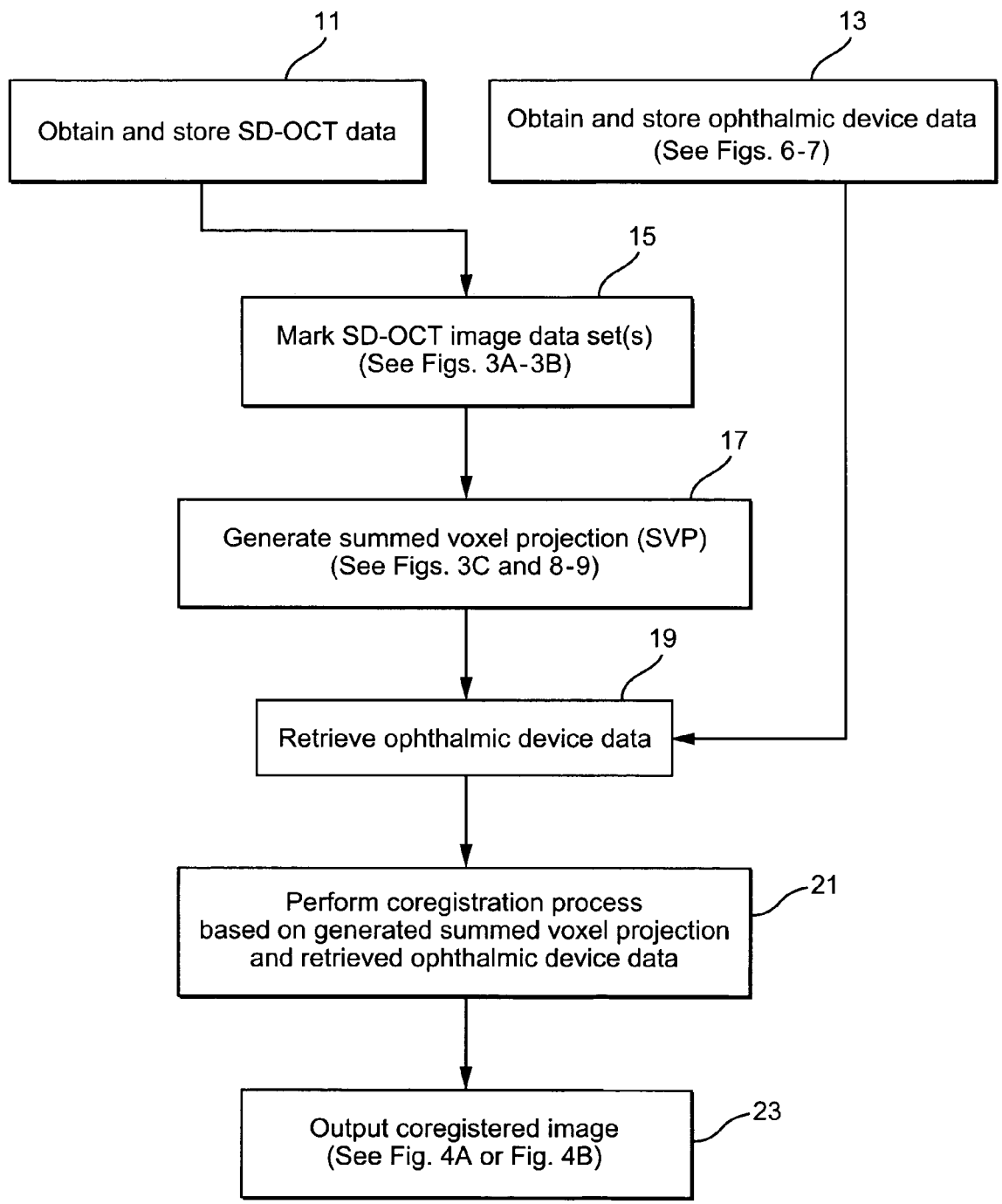
FIG. 2 is a flowchart illustrating a process for co-registrating a SVP image of marked SD-OCT image data with an image from other imaging device(s) such as ophthalmic device(s) in accordance with a present exemplary embodiment.

FIG. 2 illustrates an exemplary method which may be performed using the system illustrated in FIG. 1 to annotate, extract and/or preserve different pathological conditions and/or changes that are recognized on cross-sections within a three dimensional volume (of for example, a patient's eye) so that the marked findings are maintained (visible) in an en face projection produced with a SVP technique. The method makes it possible to coregister the marked changes with other types of two dimensional en face images such as images from other ophthalmic device(s) 5. A coregistered image may therefore be generated having the marked findings maintained in a visible manner.

The exemplary method includes a step of obtaining and storing SD-OCT image data sets (step 11). For example, an SD-OCT device provides the SD-OCT image data sets to the image processing system 1 for storage. An example of providing such image data per se is presented in a clinical case example of a series of 100 eye fundus scans with a spectral domain optical coherence tomography (SD-OCT) (Nassif et al, "*In vivo human retinal imaging by ultrahigh-speed spectral domain optical coherence tomography*", Optics Letters 29:480-482 (2004)).

SD-OCT imaging of a 10 mm by 10 mm block of retina may be obtained using an SD-OCT device 3 to produce an SD-OCT image dataset, comprised of 100 two-dimensional B-scans, via commercial capture software (Bioptigen, Research Triangle Park, NC) executed by the SD-OCT device 3. These B-scans are exported into ImageJ software (Abramoff et al, "*Image Processing with ImageJ*", Biophotonics International 11(7):36-42 (2004)) for processing. For obtaining the SD-OCT data set, the SD-OCT light source of the SD-OCT device 3 may be a superluminescent diode (SLD) from Superlum, Ltd. with central wavelength of 840 nm and bandwidth of 49 nm. The power incident on the patient's cornea may be roughly 500 µW, which is well below the ANSI extended exposure limit of 700 µW for 8 hours. (See Zawadzki R J, Jones S M, Olivier S S, et al., "*Adaptive-optics optical coherence tomography for high-resolution and high-speed 3D retinal in vivo imaging*," Optics Express 2005;17: 8532-46.) Each A-scan covers approximately a 20 micron diameter site.

As one example of obtaining the SD-OCT data set for each eye, a retinal area of 10 mm by 10 mm or 12 mm by 12 mm is imaged in 5.8 seconds in a series of 100 horizontal SD-OCT scans containing 1000 A-scans in each B-scan. This produces 100 B-scans with oversampling laterally and 80 to 100 micron spacing between B-scans. Bioptigen SD-OCT software (version 1.2, Bioptigen Inc., Research Triangle Park, NC) executed by the SD-OCT device 3 may be used for all image capture. In addition to imaging the macula, the series of scans may include the temporal border of the disc and the temporal arcades. In several eyes, two patterns of additional scans are captured: first the scans followed the same sampling as above except that they were oriented 90 degrees to the horizontal; and second a 5 mm by 5 mm area is imaged with 200 horizontal B-scans of 500 A-scans each, resulting in 25 micron spacing between scans. Each image set is captured in 5.8 seconds.

The image processing system 1 also receives and stores image data from one or more ophthalmic devices such as an angiography device, an autofluorescence device, a fundal photography device and/or a microperimetry device (step 13). FIGS. 6A-6E and 7A-7D illustrate example images generated from such data. This image data may be obtained before, after or at the same time as the SD-OCT image data is obtained, but preferably within a time before any pathologic condition shown in one of the images has changed.

After stacks of the horizontal SD-OCT B-Scans are imported to the ImageJ software executed by the image processing system 1 (or alternatively by the SD-OCT device 3), one or more of the image data sets is marked (step 15). In the foregoing example, one or more of the 100 image data sets, each representing one SD-OCT B-scan, may be marked to indicate any particular pathological condition of interest. These markings of pathology can be prepared manually through input by the user on user interface 7, through computer image algorithms executed by the image processing system 1, or through a combination of these two. The process of delineating pathological conditions may therefore be partially or fully automated using image processing, rendering and interpolation algorithms. For example, all hyporeflective sites within retinal area may be marked in one color by a computer algorithm for cystoid macular edema or by a marking of each cyst with a particular (different) color from the user. In this particular case, the presence and location of pathology is marked manually by a user/examiner (e.g., ophthamlogist or supervised research associate (ED) trained in OCT reading and annotation methods) on each of the 100 SD-OCT scans (see, e.g., FIGS. 3A-3B) delinating the pathology on the stacks of B-scans in ImageJ. For example, retinal pathology visible on SD-OCT scans may be marked on each side as follows (see FIGS. 3A-3B and FIGS. 8A-8G for examples of the color marking):

- margin of CNV at the RPE (red): the site of interruption of the normal RPE reflex at the edge of a subretinal lesion that is not a drusen, a PED or geographic atrophy;
- margin of pigment epithelial detachment (PED) at the RPE (orange): the margins of elevation of the RPE for a lesion greater than that of the largest soft drusen;
- cystoid macular edema (yellow): intraretinal rounded lesions of greater than 10 contiguous pixels of low reflectivity, not in a vertical line (not a shadow);
- macular edema without cysts (dark green): thickening of the retina relative to adjacent area;
- margins of subretinal fluid (blue): areas of very low reflectivity between the photoreceptors and the RPE;
- horizontal extent of drusen cross-section (magenta): small elevations of the pigment epithelium consistent with drusen and not reaching the size of PED;
- Horizontal extent of cross-section of fine, indistinct drusen (teal green): very small elevations of the RPE that are too small to show a definite lesion beneath the RPE; and Horizontal extent of geographic atrophy (light purple): areas of transmitted high reflectivity deeper into the choroid with well-defined margins.

Through appropriate marking of the SD-OCT scans by the user and/or computer image algorithm, annotation data indicating the type and location of a pathological condition on a respective SD-OCT scan is generated. In addition to the type and location of the pathological condition on an SD-OCT scan, the annotation data may also indicate a severity, size, surface area, thickness and/or volume of the pathological condition. For example, a user and/or computer image algorithm may determine that a part of an eye in an SD-OCT scan has a very severe pathological condition, while another part of the eye in that SD-OCT scan is benign. The user and/or algorithm input these determinations, and corresponding annotation data is generated. On the basis of this annotation data, an appropriate coloring of the marks on the SD-OCT scan may be generated. For example, the severe pathological condition of one part of the eye may be represented on the SD-OCT scan by a shade of one color, while the benign condition of the other part of the eye is represented on the SD-OCT scan with another shade of the same color or a completely different color. Accordingly, the coloring of the marking on the SD-OCT scans varies based on the annotation data relating to severity as determined by the user and/or algorithm.

As another example, a user and/or computer image algorithm may quantitatively determine that a pathological condition of a part of an eye in an SD-OCT scan has a certain thickness (thickness A) extending in an axial direction with respect to the scan, while the pathological condition of another part of the eye in that same SD-OCT scan has a different axial thickness (thickness B). The user and/or algorithm input these determinations, and corresponding annotation data is generated. On the basis of this annotation data, an appropriate coloring of the mark(s) on the SD-OCT scan may be generated. The coloring of the mark(s) corresponding to the pathological condition having thickness A will be represented on the SD-OCT scan by a shade of one color, while the coloring of the mark corresponding to the pathological condition having thickness B will be represented on the SD-OCT scan with another shade of the same color or a completely different color. (See, e.g., FIG. 10A). Accordingly, the coloring of the marking on the SD-OCT scans varies based on the annotation data relating to axial thickness of the pathological condition as determined by the user and/or algorithm. The input by the user and/or algorithm may be a qualitative or quantitative assessment of the pathological condition.

Figure 10A:
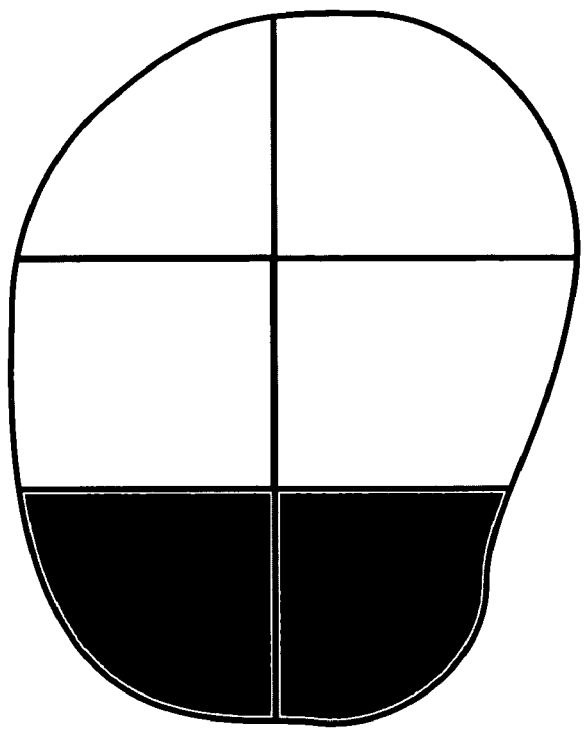
FIG. 10A shows a pathological condition in an SD-OCT scan that is represented by different colors or different shades of a color which vary based on annotation data resulting from user and/or image algorithm input. The colors or different shades of color are preserved in the SVP and coregistration images based on this scan.
Figure 10B:
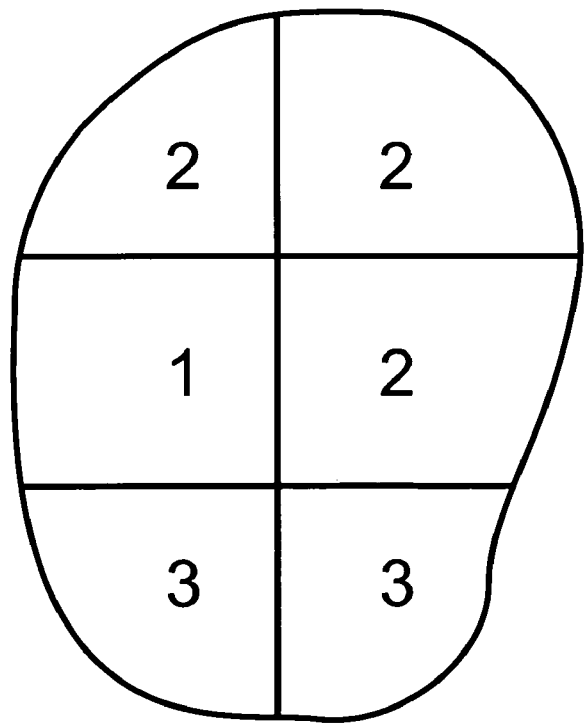
FIG. 10B shows a pathological condition in an SD-OCT scan that is represented by a set of numbers whose respective values vary based on annotation data resulting from user and/or image algorithm input. The values are preserved in the SVP and coregistration images based on this scan.

As an alternative to the coloring of the marking on the SD-OCT scan varying based on annotation data, a set of numbers may be used to represent a pathological condition. The value of each number in the set may vary based on the annotation data. As an example, FIG. 10A shows a pathological condition of the SD-OCT scan illustrated in FIG. 8A in which the darkest shade of a color indicates a pathological condition having an axial thickness A, a medium shade of the color indicates the pathological condition having an axial thickness B (thickness A being greater than thickness B), and a light shade of the color indicates the pathological condition having an axial thickness C (thickness B being greater than thickness C). FIG. 10B shows the same pathological condition, but in this case, the pathological condition is representative by a set of numbers whose values vary with axial thickness. In particular, the parts of the pathological condition having the thickness A is represented by the number "3", the parts of the pathological condition having the thickness B is represented by the number "2", and the part of the pathological condition having the thickness C is represented by the number "1".

Figure 3A:
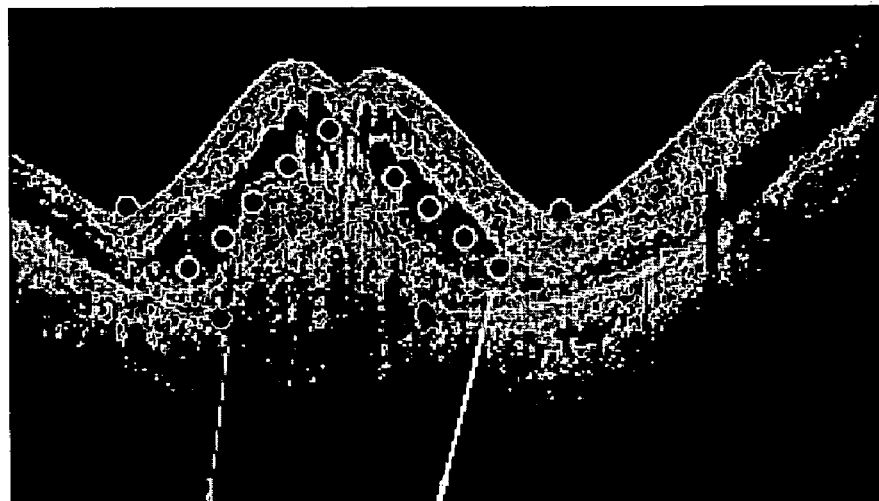
FIGS. 3A-3B are examples of SD-OCT B-scans through the foveola (FIG. 3A) and across a subretinal fluid (FIG. 3B). Borders of CNV (red), CME (yellow), ME without cysts (green) and subretinal fluid (blue) are landmarked on each scan via a user (e.g., ophthalmologist) and/or processing system.
Figure 3C:
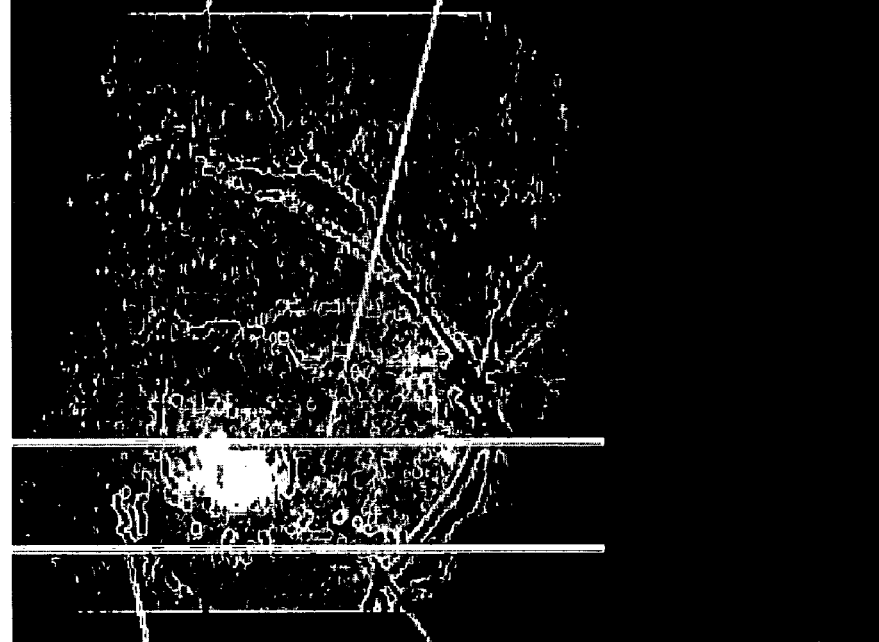
FIG. 3C is an image of a summed voxel projection (SVP) of the SD-OCT data of the scans illustrated in FIGS. 3A-3B including color marking (faint color) demonstrating en face location of the pathology. Accordingly, the color marking in the SD-OCT scans of FIGS. 3A-3B are maintained in the SVP of FIG. 3C.

The three-dimensional block of scans is then flattened or collapsed to thereby generate the summed voxel projection (SVP) through execution of the image processing system 1 (step 17; see FIG. 3C). The SVP process per se may be performed for example in accordance with Jiao et al, Optics Express 13:444-452 (2005). The SVP, in accordance with present exemplary embodiments, retain the colored (or numbered) marks of pathology entered or generated in step 15 relative to retinal vascular landmarks. The SVP of the SD-OCT data plus the color (or number) markings displays the type, location, size, surface area, thickness, volume and/or severity of all marked pathologies integrated in one en face image. This part of analysis may be developed on the stack of images by execution, for example, of the ImageJ program by the system 1. Other imaging software programs or algorithms may alternatively be used. During execution of the ImageJ program to generate the SVP, typical steps include executing a reslice function followed by a dimensional projection using average pixel intensities of the image stack in ImageJ. The quality of the resulting en face SVP image can be further improved by enhancing contrast and color or other parameters with ImageJ or other software or algorithms.

Figure 3B:
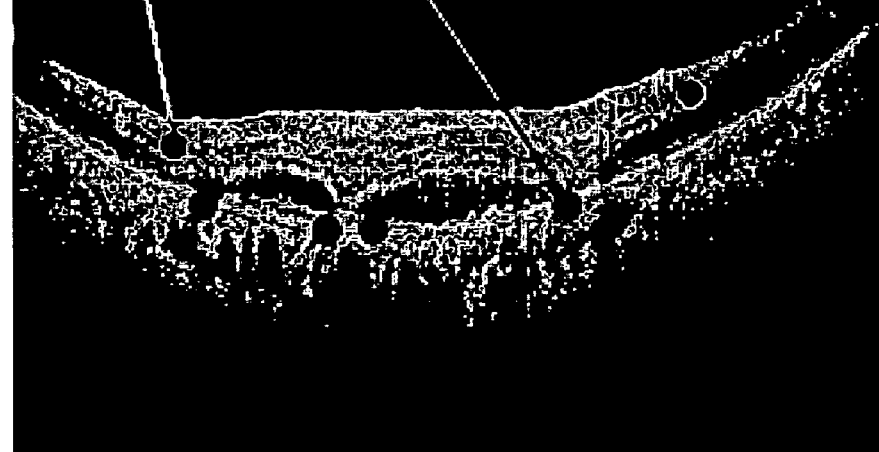

Further processing by ImageJ execution by the system 1 includes executing the image/stacks/reslice function followed by the image/stacks/Z-project function using the sum slices projection type, which sums pixel intensities. As illustrated in FIGS. 3A-3B, SD-OCT images may be in grayscale, while all annotation is in color. As illustrated in FIG. 3C, the color annotation in the SD-OCT images of FIGS. 3A-3B are visible in the SVP in contrast to the grayscale summed OCT data. The resulting en face images may have a resolution of 1000 pixels horizontally and 100 pixels vertically, and therefore may be stretched vertically by factor 10 to obtain a square image of 1000 by 1000 pixels that represents a fundus image of the 10 mm by 10 mm retinal block scanned with color markings preserved. The contrast of the retinal vessel pattern and the intensity of the color annotations were improved by enhancing contrast and color of the SVPOCT images. The markings of the SVP may be further processed so that they appear as a contiguous line (see, e.g., the solid colored lines shown in FIGS. 4A-4B as opposed to the colored "dots" illustrated in the SVP of FIG. 3C) or a continuous area. The continuous area represents for example the lateral area of the pathology.

The stored image data from the ophthalmic device(s) is retrieved (step 19). While FIG. 2 shows this retrieval step being performed after steps 15 and 17, step 19 may alternatively be performed prior to steps 15 and 17. The image processing system 1 then performs a coregistration process (step 21) based on the retrieved image data from the ophthalmic device(s) and the image data of the SVP (including markings) generated in step 17. The coregistration process involves properly aligning the images formed from the ophthalmic device data and the SVP. Proper alignment may be based on one or more common point (e.g., vascular landmark) identified in each of the images and may include for example re-scaling the size of, stretching or compressing one or more of the images. Once the images are properly aligned, they are then superimposed together including the markings of the SVP. For example, the en face SVP image with preserved color markings is superimposed on an en face fluorescein angiography image (resulting in the coregistered image of FIG. 4A having preserved color markings) or an en face microperimetry image (resulting in the coregistered image of FIG. 4B having preserved color markings) using vascular landmarks. The coregistered image may then be output (step 23) by displaying it on display 9, printing a hard copy and/or transmitting to another device etc.

In performing the coregistration process (step 21), either Adobe Photoshop (Adobe Photoshop version 7.0, Adobe Systems, San Jose, Calif.), GNU Image Manipulation Program (GIMP version 2.2, Free Software Foundation Inc., Boston, Mass.), or ImageJ UnwarpJ plugin (UnwarpJ, Biomedical Imaging Group-Swiss Federal Institute of Technology Lausanne, Switzerland) may be executed by the image processing system 1 to overlay and align images. The en face SVPOCT image with preserved color markings is superimposed on fundus images from other studies using vascular landmarks for alignment and warping of the SVP as required to match up the retinal vascular patterns. The color annotation and margins of the overlay are left intact as the gray image layer of the SVPOCT may be deleted to leave the color annotation aligned over the fundus image and data of the other studies (i.e., studies performed in step 13). These other retinal studies may include: color fundus photographs, fluorescein angiograms, autofluorescence imaging (Heidelberg Retina Angiograph 2, Heidelberg Engineering, Smithfield, R.I.) and microperimetry testing (MP-1, Nidek, Freemont, Calif.). The microperimetry testing may be performed using a Goldman 3 size white light test object with 4-2-1 step testing with the retinal sensitivity recorded being the highest number of decibels of neutral density filtering at which the patient still responds, and zeroes with filled blocks meaning no response to the brightest illumination.

The present exemplary embodiments preserve important information previously identified and marked that is lost in en face images obtained by collapsing three dimensional volumes to a two dimensional plane in a conventional way. This allows coregistration of pathology from OCT into en face tests of function (e.g., microperimetry) or perfusion (e.g., fluorescein angiogram). The present exemplary embodiments could also be used in OCT imaging outside the eye.

Clinical Results Obtained Through Present Exemplary Embodiments

In a series of 12 eyes with AMD, components of the macular lesions were imaged in cross-section with SD-OCT and the information was annotated in color on the scans in accordance with present exemplary embodiments, transferred into two-dimensional en face images and correlated with other clinical data. These techniques were useful to identify and mark neovascular (5 eyes) and non-neovascular (7 eyes) AMD lesion components, including drusen, geographic atrophy, pigment epithelial detachment, subretinal and intraretinal fluid, and thickening or thinning of retinal layers, as demonstrated in FIGS. 3-4 and 7-9. Six of these 12 eyes were phakic with mild to notable cataracts present in these eyes. In this series, SD-OCT imaging was not prevented by cataract. Examples of data, observations and findings obtained using present exemplary embodiments, including preserving annotation data of pathologic features for en face SVP images and coregistered images using the SVP image and other image data, are discussed below (Patients 1 and 2).

Patient 1

Figure 5:
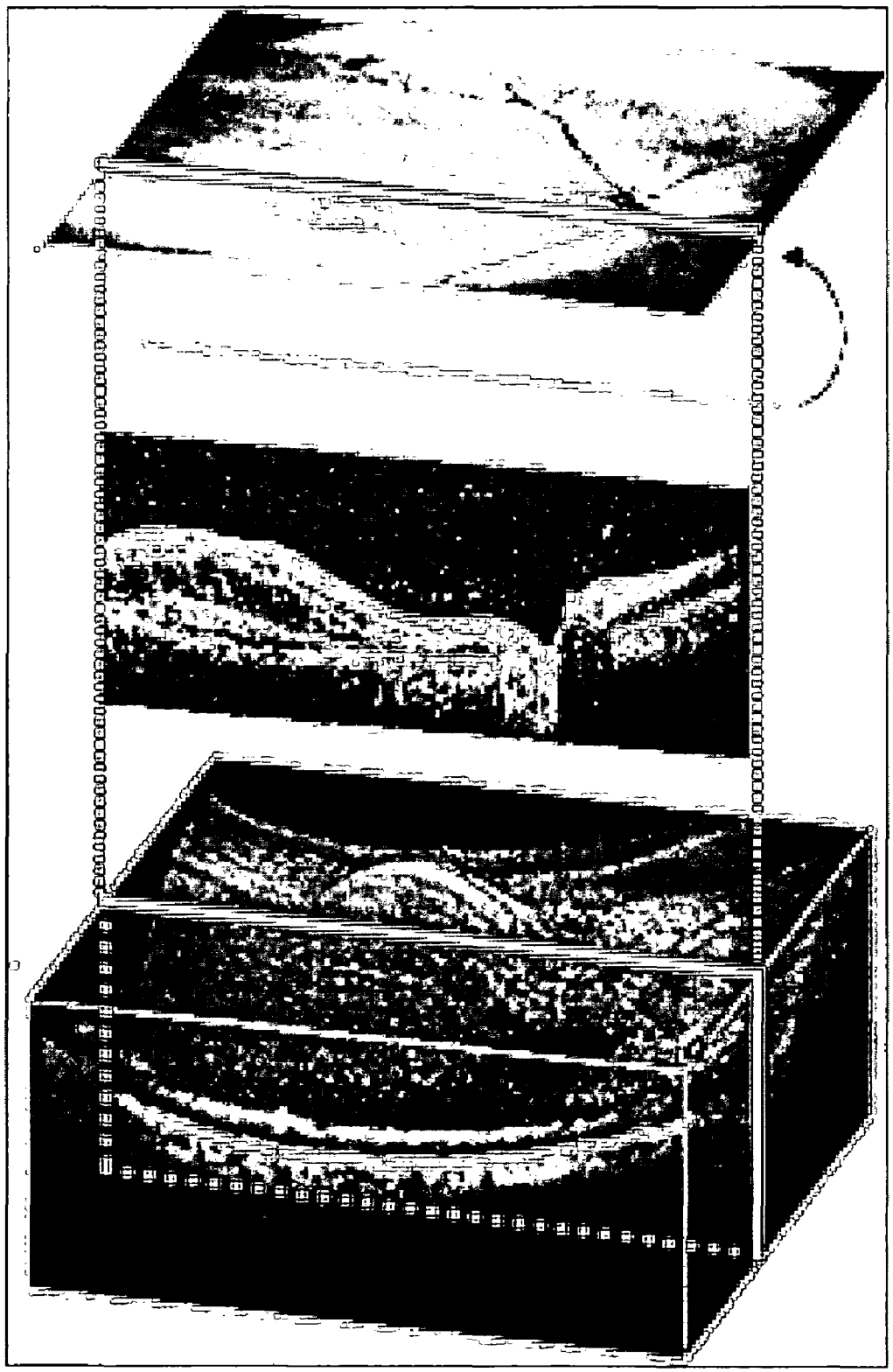
FIG. 5 is an unannotated summed voxel projection (SVP) fundus image (top) of patient 1 created by collapsing along the Z-axis of a 3D volume (bottom). The 3D volume was created from 100 B-scans (middle). Because of the speed of spectral domain OCT imaging, the 100 scans were obtained in under 6 seconds. In the SVP, a single B-scan (middle) projects to a line of data in the surface/sum projection (top).

Patient 1 is a 69 year old female with age related macular degeneration and subfoveal choroidal neovascularization (CNV) in the right eye presented with continued decrease in visual function and acuity (20/100) 6 weeks after a single injection of 0.3 mg pegaptanib sodium (FIG. 6). An unmarked stack of 100 SD-OCT scans could be collapsed along the z-axis to create the summed voxel projection. (See FIG. 5 showing a SVP of SD-OCT B-scans which do not have annotation data). The pathologic findings were marked on each B-scan in the SD-OCT stack and then the same process was repeated producing an en face image from the OCT scans and showing the extent of CNV, cystoid macular edema, macular edema without cysts and subretinal fluid (FIG. 3C). In this eye, early hyperfluorescence on fluorescein angiography corresponded with CNV area on an en face image from SD-OCT, but subretinal fluid was not visible on the fluorescein angiogram imaged out to 6 minutes (FIG. 4A). In contrast, both macular edema and subretinal fluid were mapped from SD-OCT to areas extending many hundreds of microns beyond the margins of the CNV visible on the fluorescein angiogram (FIG. 4A). Both retinal thickening and subretinal fluid corresponded closely with areas of no response to the brightest Goldmann 3 stimulus on microperimetry (FIG. 4B).

Patient 2

Patient 2 is a 72 year old female with bilateral drusen and geographic atrophy presented with a decrease of vision in the right eye for 4 weeks. Her visual acuity was 20/40 in the right eye. The patient has multiple large drusen in the macula: some drusen are soft, some confluent with pigmentation, few are intensely autofluorescent and some stain with fluorescein dye (FIGS. 7C-7D). In the SD-OCT image, the size of distinct, discrete and indistinct, coalesced drusen and geographic atrophy can be differentiated (FIG. 8). Because a cross-section of each druse could be compared focally to the corresponding site in the autofluorescence map, the cross-sectional patterns of drusen at the two most prominent sites of anomalous increase in autofluorescence were identified (arrows FIG. 7B). At site #1, the increased autofluorescence corresponded to a drusen with high reflectivity at the inner surface and high reflectivity extending into the overlying retina (FIG. 8D). At site #2, in contrast, the increased autofluorescence corresponded to an unusual OCT reflectivity pattern within the druse (FIG. 8F). In the SD-OCT, there was focal increased reflectivity within the druse in half of its cross-section, while the other half had a more normal lower reflectivity. At this site, there was no overlying increase in reflectivity within the retina.

Although patient 2 had cataracts which dimmed the color photographic images of drusen and GA (FIG. 7A), the borders of drusen and geographic atrophy were still clearly discernible in the SD-OCT scans (FIGS. 8D and 8F). This is because the OCT imaging was based on a change in a location of signal (elevation of reflectivity at the site of drusen or deeper extent of high reflectivity at sites of geographic atrophy) unlike the color photographs that depend on contrast of yellow color of drusen to darker adjacent tissue. Although the overall OCT signal could be decreased due to cataracts, the location of signal from elevated drusen remains unchanged.

Improving Sampling of Focal Pathology

In the examples (patients 1 and 2) above, 100 lateral scans covered a 10 mm by 10 mm area and thus the SVP images had lower vertical sampling density (from inferior to superior arcade) of 100 pixels of 20 microns in diameter across 10-12 mm (80 to 100 microns between samples), as opposed to horizontal sampling density of 1000 pixels of 20 microns in diameter across 10-12 mm (overlapping sampling). These sampling conditions can be adjusted to improve sampling density and thus the resolution of the scan so as to capture focal pathology such as drusen with the same short duration of data capture. To improve the vertical resolution, a greater number of scans over a smaller area (200 scans of 500 A scans each, over a 5 mm by 5 mm scan area) were captured over the same short capture time of 5.7 seconds to improve the SVP images and overall resolution for imaging of drusen. When compared to the lower density scan pattern of the 10 mm by 10 mm scans, the higher density scan pattern provided better resolution of the pattern of small retinal vessels in the SVP image which allowed alignment of macular images with corresponding retinal data without requiring imaging of larger vessels of the arcades for overlay (FIG. 9A and 9C). In addition, using the image processing methods described above, one could readily identify small to moderate size drusen to overlay with fundus data (FIGS. 9B and 9D). With both methods of SD-OCT scanning in eyes with non-neovascular AMD and drusen on clinical examination, focal subretinal fluid was found on SD-OCT analysis at the fovea over the drusenoid PED (FIG. 9F). This was not identified on FA (FIG. 9E) or conventional OCT scans.

In neovascular AMD, the SD-OCT-imaged pathology corresponded to areas where no specific pathology was visible on conventional digital fluorescein angiography. In addition, the SD-OCT-mapped pathology corresponded with sites of pronounced decrease in retinal sensitivity. In the three patients with subretinal fluid, the full extent of subretinal fluid was not appreciated on digital fluorescein angiography, but was readily mapped from the SD-OCT (FIG. 4A). Although retinal thickening or subretinal fluid could have been appreciated in examination of stereo color photographs or stereo fluorescein angiograms, differentiating subretinal fluid from intraretinal thickening would be difficult with these methods. (See Bressler N M, Bressler S B, Alexander J, et al., "*Loculated fluid. A previously undescribed fluorescein angiographic finding in choroidal neovascularization associated with macular degeneration,*" Macular Photocoagulation Study Reading Center. Arch Ophthalmol 1991;109:211-5; and Soubrane G, Coscas G, Larcheveque F., "*Macular Degeneration related to age and cystoid macular edema [in French],*" Apropos of 95 cases (100 eyes). J Fr Ophthalmol 1988;11:711-20.) The area of intraretinal cysts, mapped from the SD-OCT, correlated with late faint hyperfluorescence in each eye. Very poor retinal sensitivity on microperimetry (no response to the brightest stimulus) extended across not only the extent of CNV complex in 3 eyes, but also across the areas of intraretinal cysts, subretinal fluid and intraretinal thickening (FIG. 4B).

In non-neovascular AMD, discrete and indistinct, coalesced drusen and geographic atrophy identified on SD-OCT could be superimposed on color fundus photographs and on autofluorescence imaging (FIGS. 8-9). Different patterns of drusen were identified on the SD-OCT scans and unusual patterns of high reflectivity within drusen or extending into the retina over drusen appeared to correlate with increases in autofluorescence in this series. As will be appreciated from the different sized markings in FIG. 8A, the drusen may have different thicknesses, sizes, en face area and/or volume. In 2 eyes, very small foci of low reflectivity that may represent subretinal fluid was seen in eyes with coalescent soft drusen and drusenoid PED. This was not suspected prior to the SD-OCT scan (FIG. 9F).

Discussion

Direct and indirect ophthalmoscopy, fluorescein angiograms and other tests provide clinicians with en face images of the retina. Many treatment options such as laser therapy are based on the en face fundus images. Therefore, coregistration of pathology delineated on OCT images with the en face fundus images is of clinical importance.

Combining scanning laser ophthalmoscope (SLO) with OCT (SLO/OCT) attempts to address this issue. (See Podoleanu A G, Dobre G M, Cucu R G, et al., "*Combined multiplanar optical coherence tomography and confocal scanning ophthalmoscopy,*" J Biomed Opt 2004;9:86-93. Van Velthoven M E J, de Vos K, Verbraak F D, et al., "*Overlay of conventional angiographic and en-face OCT images enhances their interpretation,*" BMC Ophthalmol 2005;5:12; Van Velthoven M E J, Verbraak F D, Garcia P M, et al., "*Evaluation of central serous retinopathy with en face optical coherence tomography,*" Br J Ophthalmol 2005;89:1483-8; Van Velthoven M E J, Verbraak F D, Yannuzzi L, et al., "*Imaging the retina by en face optical coherence tomography,*" Retina 2006;26:129-36; and Podoleanu A G, Rogers J A, Jackson D A, "*3D OCT images from retina and skin,*" Optics Express 2000;7:292-8.) The images produced in SLO and OCT channels are in strict pixel-to-pixel correspondence. However, this is a time domain not spectral domain system, and thus is relatively slow (2 frames per second). Fundus images from the SLO channel, even though of high transverse resolution, are able to show only superficial changes registered by SLO channel. (See Van Velthoven M E J, de Vos K, Verbraak F D, et al., "*Overlay of conventional angiographic and en-face OCT images enhances their interpretation,*" BMC Ophthalmol 2005;5:12.) Deeper layers with possible clinically relevant lesions are visible in transverse C-scans which are built up from several parallel B-scans and are viewable along Z-axis. (See Podoleanu A G, Rogers J A, Jackson D A, "*3D OCT images from retina and skin,*" Optics Express 2000;7:292-8.) Unfortunately, C-scans show successive concentric inner and outer layers due to curvature of the eye. Real borders of the potential lesion can therefore exceed those visible at one particular C-scan. As a consequence, superimposed C-scan images on fluorescein angiograms, as described previously, do not necessarily show real extension of the lesions in relation to angiographic findings. (See Van Velthoven M E J, de Vos K, Verbraak F D, et al., "*Overlay of conventional angiographic and en-face OCT images enhances their interpretation,*" BMC Ophthalmol 2005;5:12; Van Velthoven M E J, Verbraak F D, Garcia P M, et al., "*Evaluation of central serous retinopathy with en face optical coherence tomography,*" Br J Ophthalmol 2005;89:1483-8; and Van Velthoven M E J, Verbraak F D, Yannuzzi L, et al., "*Imaging the retina by en face optical coherence tomography,*" Retina 2006;26:129-36.) Furthermore, images of a lesion from a C-scan may be more difficult to define and interpret than images from a B-scan, even for an experienced clinician.

Spectral domain OCT enables one to perform a large number of scans over a selected region of retina and to rapidly collect a large quantity of clinically important data. Until now, the data within the scans was not integrated with information on exact location and extension of the pathology on a conventional fundus image. Although it is possible to create three-dimensional retinal images that allow visualization of retinal microstructures (video image) (See Zawadzki R J, Jones S M, Olivier S S, et al., "*Adaptive-optics optical coherence tomography for high-resolution and high-speed 3D retinal in vivo imaging,*" Optics Express 2005;17:8532-46.), this method is not very useful for several reasons. First, the 3D stack is a large dataset and thus difficult or slow to transfer in a clinical setting compared to 2D images. Second, the 3D images are not aligned with other fundus data, such as angiograms, etc., and thus are viewed in isolation. Third, clinicians are used to working with en face images or B-scans.

Converting a stack of SD-OCT B-scans to C-scans has the same limitation as described above for SLO/OCT systems. The plain summed voxel projection as described by Jiao at al. (See Abramoff M D, Magelhaes P J, Ram S J, "*Image Processing with ImageJ,*" Biophotonics International 2004;11:

36-42.), that results in a fundus image produced by collapsing three dimensional volumes to a two dimensional plane along the depth axis, clearly loses most information that might be relevant for the diagnosis and therapy. Segmenting fewer layers from a 3-dimensional OCT image and then collapsing into the summed voxel projection may preserve more pathologic features, but delineation of pathologic features is still degraded in contrast to the full 3-dimensional data set. This process is complex due to the curvature of the layers of interest. Even though borders of highly reflective large lesions such as subretinal scars are identifiable on plain SVP images, less prominent features such as cysts, edema, subretinal fluid, and drusen may not be visible. This is because most information is lost when a stack of unmarked B-scans is averaged along the depth axis to calculate a single representative pixel along each line.

The present exemplary embodiments, which relate to pathology delineation and integration with summed voxel projection (SVP), enable the clinician to visualize the extent of lesion components, drusen edema, subretinal fluid and any other feature that can be marked in the process of interactive image evaluation by a trained OCT grader. All marked pathologies can be integrated in one en face fundus image that can serve as a reference for further diagnosis and therapy or can be combined with results of other perfusion or functional tests (FIGS. 3-4 and 7-8). One can superimpose en face SVP images including preserved color (or number) markings on fluorescein angiograms and microperimetry, using vascular landmarks. Image processing of present exemplary embodiments results in a useful annotated fundus image that clinicians and researchers can use for comparison with other conventional data, or potentially to monitor pathology over time. With the denser pattern of scanning over the macula, such as with the example of the 5 mm scans (FIG. 9), the vascular pattern around the macula is imaged in the SVP at a resolution useful for overlay of this focal image over corresponding retinal data. This eliminates the need to capture larger SVP images so as to include large retinal vessels for registration of images, and thus saves on the size of high resolution datasets. These higher density scans of the macula will be useful in measuring drusen numbers and volumes for phenotypic studies of AMD.

The ophthalmic imaging and OCT image analysis techniques of the present exemplary embodiments preserve important information that is identified in the three-dimensional data set, but that has been heretofore lost when the three-dimensional volume is collapsed to produce the two-dimensional SVP image. (See Abramoff M D, Magelhaes P J, Ram S J, "*Image Processing with ImageJ*," Biophotonics International 2004;11:36-42.) This technique has not heretofore been implemented in ophthalmic imaging with optical coherence tomography. These present methods allow coregistration of pathology from OCT into en face tests of function (e.g. microperimetry) or perfusion (e.g. fluorescein angiography) to enable understanding of the factors involved in vision loss in AMD and other ophthalmic diseases to be improved. With SD-OCT scanning configured for higher resolution, focal macular pathology such as drusen can be coregistered with color fundus photographs or autofluorescence images. These measures may be used to monitor disease progression over time.

SD-OCT imaging of the posterior pole may therefore be obtained in patients with neovascular and non-neovascular age-related macular degeneration area, thickness and/or severity (AMD), creating three-dimensional stacks of images. The type, location, size, en face surface area, thickness and/or severity of pathology may delineated with color or numerical markings in each SD-OCT scan before the stack of scans was collapsed along the depth axis in a SVP process. This en face image may contain dark lines at sites of retinal vessel shadowing and preserves color or numerical markings of delineated pathology relative to the vessel pattern. The SVP image may then be superimposed onto other 2-D images and data from other studies of these eyes. Each of the 2-dimensional images may be "mapped" on a flat or on a non-planar surface such as a curved surface (e.g., curved in the axial direction).

As described above, beneficial clinical results have been obtained using present exemplary embodiments. For example, in patients with neovascular AMD, the location and extent of CNV, cystoid macular edema, macular edema without cysts, and subretinal fluid were visible on the two dimensional summed images and in some cases involved sites not suspected with conventional imaging. In patients with non-neovascular AMD, the location, extent, and patterns of drusen and geographic atrophy were correlated with sites of increase or decrease in autofluorescence. In one eye with drusen and in three eyes with neovascular AMD, the presence or extent of subretinal fluid identified on SD-OCT was not visible using other imaging methods.

In accordance with present exemplary embodiments, pathology within SD-OCT scans may delineated and transferred into two-dimensional en face projections enabling researchers to associate lateral extent of pathology (as well as other pathological features such as type, location, size, thickness and/or severity) from SD-OCT to corresponding other studies. This integration of SD-OCT imaging with other retinal studies enables further study of the relationship between local OCT morphology and other parameters of retinal disease or retinal function in diagnosis and therapy.

While the invention has been described in connection with what is presently considered to be practical exemplary embodiments, it is to be understood that the invention is not limited to the disclosed embodiments, but, on the contrary, is intended to cover all variations, modifications and equivalent arrangements included within the spirit and scope of the appended claims.

What is claimed is:

1. A method comprising:
   receiving, in a computer system, optical coherence tomography (OCT) data;
   generating, using the computer system, first image data corresponding to a summed voxel projection (SVP) of the received OCT data;
   receiving, in the computer system, second image data obtained with at least one ophthalmic device, the second image data representing a data set independent from the OCT data and the first image data; and
   coregistrating, using the computer system, the first image data and the second image data to generate coregistered image data.

2. The method of claim 1 wherein the at least one ophthalmic device is an angiography, microperimetry, fundus autofluorescence and/or fundus photography device.

3. The method of claim 1 wherein coregistrating the first image data and the second image data includes identifying a common point on images respectively corresponding to the first image data and the second image data to align the first image data and the second image data.

4. The method of claim 1 further comprising receiving, in the computer system, annotation data associated with the OCT data and preserving the annotation data in the first image data when generating the first image data corresponding to the SVP.

5. The method of claim 4 further comprising preserving, using the computer system, the annotation data in the coregistered image data when coregistrating the first image data and the second image data.

6. The method of claim 4 wherein the annotation data identifies a location of a pathological condition in the first image data.

7. The method of claim 4 wherein the annotation data identifies a size, surface area, thickness and/or volume of a pathological condition in the first image data.

8. The method of claim 4 wherein the annotation data identifies a severity of a pathological condition in the first image data.

9. The method of claim 4 wherein the annotation data is represented in a first image resulting from the first image data as a color coded marking.

10. The method of claim 9 wherein colors of the color coded marking vary in accordance with one or more of the following features of a pathological condition: size, surface area, thickness, volume and severity.

11. The method of claim 4 wherein the annotation data is represented in a first image resulting from the first image data as a set of numbers.

12. The method of claim 1i wherein values of the set of numbers each varies in accordance with one or more of the following features of a pathological condition: size, surface area, thickness, volume and severity.

13. The method of claim 4, wherein the annotation data is user-defined annotation data.

14. The method of claim 1 further comprising:
receiving, in the computer system, annotated data associated with the OCT data and preserving the annotated data in the first image data when generating the first image data corresponding to the SVP;
preserving, using the computer system, the annotated data in the coregistered image data when coregistrating the first image data and the second image data; and
processing, using the computer system, the coregistered image data so that the annotated data is represented as a contiguous line or a continuous area on a coregistered image.

15. A method comprising:
receiving, in a computer system, a plurality of image data sets, each image data set representing an OCT scan and annotation data associated with a part of that represented OCT scan;
performing, using the computer system, a summed voxel projection (SVP) of the plurality of image data sets to generate a first image having a marking corresponding to the annotation data;
aligning, using the computer system, the first image with a second image obtained using at least one ophthalmic device, the second image being generated from a data set independent from said each image data set representing an OCT scan; and
superimposing, using the computer system, the first and second images together to generate a third image, the third image having the marking corresponding to the annotation data.

16. The method of claim 15 wherein the annotation data associated with the part of that represented OCT scan indicates a location of a pathological condition.

17. The method of claim 15 wherein the annotation data associated with the part of that represented OCT scan indicates a size, surface area, thickness and/or volume of a pathological condition.

18. The method of claim 15 wherein the annotation data associated with the part of that represented OCT scan indicates a severity of a pathological condition.

19. The method of claim 15 wherein the marking on the first image is a color coded marking.

20. The method of claim 19 wherein colors of the color coded marking vary in accordance with one or more of the following features of a pathological condition: size, surface area, thickness, volume and severity.

21. The method of claim 15 wherein the marking on the first image is represented in the first image as a set of numbers.

22. The method of claim 21 wherein values of the set of numbers each varies in accordance with one or more of the following features of a pathological condition: size, surface area, thickness, volume and severity.

23. The method of claim 15 wherein the second image is generated by performing one or more of the following: micropenmetry, angiography, autofluorescence and color fundus photography.

24. The method of claim 15 wherein a plurality of the image data sets have annotation data associated with a part of a respective OCT scan so that the first and third images each has a plurality of marks.

25. The method of claim 24 further comprising processing the third image so that the marks will appear as a contiguous line or a continuous area.

26. The method of claim 15, wherein the annotation data is user-defined annotation data.

27. An image processing system comprising:
a first input that receives optical coherence tomography (OCT) data;
a second input that receives image data obtained with at least one ophthalmic device, the image data obtained with the at least one ophthalmic device representing a data set independent from the OCT data; and
a processor that performs a summed voxel projection (SVP) of the OCT data to produce SVP image data, and that performs a coregistration process on the SVP image data and the image data received by the second input to generate coregistered image data.

28. The system of claim 27 wherein the at least one ophthalmic device is an angiography, microperimetry, fundus autofluorescence and/or fundus photography device.

29. The system of claim 27 wherein the processor receives annotation data associated with the OCT data, and the processor preserves the annotation data in the SVP image data when generating the SVP image data.

30. The system of claim 29 wherein the processor preserves the annotation data in the coregistered image data when performing the coregistration process.

31. The system of claim 30 wherein the processor processes the coregistered image data so that annotation data appears as a contiguous line or a continuous area in a coregistered image resulting from the coregistered image data.

32. The system of claim 29 wherein the annotation data is represented in a SVP image resulting from the SVP image data as a color coded marking.

33. The system of claim 32 wherein colors of the color coded marking vary in accordance with one or more of the following features of a pathological condition: size, surface area, thickness, volume and severity.

34. The system of claim 29 wherein the annotation data is represented in a SVP image resulting from the SVP image data as a set of numbers.

35. The system of claim 34 wherein values of the set of numbers each varies in accordance with one or more of the following features of the pathological condition: size, surface area, thickness, volume and severity.

36. The system of claim 29, wherein the annotation data is user-defined annotation data.

37. A method comprising:
receiving, in a computer system, optical coherence tomography (OCT) data;
generating, using the computer system, first image data corresponding to a summed voxel projection (SVP) of the received OCT data;
receiving, in the computer system, second image data obtained using at least one non-OCT ophthalmic device, the second image data representing non-OCT data; and
coregistrating, using the computer system, the first image data and the second image data to generate coregistered image data.

38. The method of claim 37 wherein the at least one non-OCT ophthalmic device is an angiography, microperimetry, fundus autofluorescence and/or fundus photography device.

39. The method of claim 37 wherein coregistrating the first image data and the second image data includes identifying a common point on images respectively corresponding to the first image data and the second image data to align the first image data and the second image data.

40. The method of claim 37 further comprising receiving, in the computer system, annotation data associated with the OCT data and preserving the annotation data in the first image data when generating the first image data corresponding to the SVP.

41. The method of claim 40 further comprising preserving the annotation data in the coregistered image data when coregistrating the first image data and the second image data.

42. A method comprising:
receiving, in a computer system, a plurality of image data sets, each image data set representing an OCT scan and annotation data associated with a part of that represented OCT scan;
performing, using the computer system, a summed voxel projection (SVP) of the plurality of image data sets to generate a first image having a marking corresponding to the annotation data;
aligning, using the computer system, the first image with a second image obtained using at least one non-OCT ophthalmic device, the second image being generated from non-OCT data; and
superimposing, using the computer system, the first and second images together to generate a third image, the third image having the marking corresponding to the annotation data.

43. An image processing system comprising:
a first input that receives optical coherence tomography (OCT) data;
a second input that receives image data obtained using at least one non-OCT ophthalmic device, the image data obtained with the at least one non-OCT ophthalmic device representing non-OCT data; and
a processor that performs a summed voxel projection (SVP) of the OCT data to produce SVP image data, and that performs a coregistration process on the SVP image data and the image data received by the second input to generate coregistered image data.

44. The system of claim 43 wherein the at least one non-OCT ophthalmic device is an angiography, microperimetry, fundus autofluorescence and/or fundus photography device.

45. The system of claim 43 wherein the processor receives annotation data associated with the OCT data, and the processor preserves the annotation data in the SVP image data when generating the SVP image data.

46. The system of claim 45 wherein the processor preserves the annotation data in the coregistered image data when performing the coregistration process.

* * * * *